United States Patent [19]

Bexten et al.

[11] Patent Number: 4,990,639

[45] Date of Patent: Feb. 5, 1991

[54] NOVEL RECOVERY PROCESS

[75] Inventors: Ludger Bexten, Hünxe; Dieter Kupies, Duisburg, all of Fed. Rep. of Germany

[73] Assignee: Hoechst AG, Werk Ruhrchemie, Fed. Rep. of Germany

[21] Appl. No.: 438,572

[22] Filed: Nov. 16, 1989

Related U.S. Application Data

[63] Continuation of Ser. No. 72,923, Jul. 14, 1987, abandoned.

[30] Foreign Application Priority Data

Aug. 16, 1986 [DE] Fed. Rep. of Germany ....... 3626536

[51] Int. Cl.$^5$ ............................................. C07F 15/00
[52] U.S. Cl. ..................... 556/136; 423/22; 502/24; 502/34
[58] Field of Search .................. 556/136; 423/22; 502/24, 34

[56] References Cited

U.S. PATENT DOCUMENTS

| | | | |
|---|---|---|---|
| 4,337,208 | 6/1982 | Petronella | 556/31 |
| 4,390,473 | 6/1983 | Cooper | 556/136 |
| 4,404,146 | 9/1983 | Lionelle et al. | 556/136 |
| 4,465,635 | 8/1984 | Chang et al. | 556/136 |

*Primary Examiner*—Gary P. Straub
*Assistant Examiner*—Stuart L. Hendrickson
*Attorney, Agent, or Firm*—Bierman and Muserlian

[57] ABSTRACT

A process for the recovery of rhodium from aqueous solutions of rhodium complex carbon atoms comprising adding a molar excess of a water-soluble salt of an organic carboxylic acid of 7 to 22 carbon atoms to an aqueous solution of a rhodium complex compound, treating the solution with an oxidant at 50° to 200° C. and recovering the rhodium as a water-insoluble compound.

9 Claims, No Drawings

NOVEL RECOVERY PROCESS

PRIOR APPLICATION

This application is a continuation of U.S. Pat. application Ser. No. 072,923, filed July 14, 1987 now abandoned.

STATE OF THE ART

DE-PS No. 2,627,354 describes a catalyst system of rhodium complex compounds and excess complex ligands to hydroformylate olefins. Under the reaction conditions, the catalyst system is formed from rhodium and a water-soluble organic phosphine used in excess Its solubility in water is due to the presence of sulfonic acid groups which are present in the organic phosphine and the phosphorus ligand is preferably used as an alkali metal sulfonate, ammonium sulfonate or alkaline earth metal sulfonate.

When the catalyst system is used over a long period, the selectivity of the reaction decreases and this fall in selectivity is due to the effects of catalyst poisons such as iron carbonyl which can form through the action of carbon monoxide on the wall of the reactor, and to higher-boiling condensation products formed from the aldehydes and to the reduction of the sulfonated phosphine used in excess by oxidation to phosphine oxides or degradation to aromatic sulfonic acids. In addition, phosphine sulfides are also formed from the phosphines and the sulfur compounds contained in the synthesis gas as well as through the reduction of sulfonic acid groups. As neither phosphine oxides nor phosphine sulfides nor aromatic sulfonic acids are desirable in the hydroformylation catalyst, it is necessary to replace the spent catalyst solution. For reasons of economy, it is necessary to remove and recover the rhodium from this catalyst solution.

DE No. 3,235,029 describes a process for the recovery of catalyst systems which are used for hydroformylation in DE-PS 2,627,354. The sulfonic acids are freed from the sulfonic acid salts by acidification and are extracted with an amine dissolved in an organic solvent, the organic phase now containing the amine salt of the sulfonated phoyphene is then removed from the aqueous solution and treated with an aqueous base and the two phases thus formed are separated. The aqueous phase now contains the rhodium complex compound and the phosphine sulfonate. A selective recovery of the rhodium from the rhodium complex compound is only possible to a limited extent as the rhodium complex compound is always obtained in unchanged form together with ligands employed in excess.

U.S. Pat. No 4,390,473 describes a process for the recovery of rhodium and cobalt from the solution of a hydroformylation catalyst dissolved in an organic solvent, triphenylphosphine being present as a ligand in said hydroformylation catalyst in addition to rhodium and cobalt complex compounds. This solution is mixed with aqueous formic acid and then oxidized with an oxygen-containing gas whereby the rhodium and cobalt complex compounds are split and the excess triphenylphosphine is oxidized. Rhodium and cobalt are transferred to the aqueous phase as formates and separated from the organic solution. The recovery of rhodium from an aqueous solution containing rhodium complex compounds is not described in the said patent.

OBJECTS OF THE INVENTION

It is an object of the invention to provide a simple and economical process for the recovery of rhodium from an aqueous solution of a rhodium complex compound.

This and other objects and advantages of the invention will become obvious from the following detailed description.

THE INVENTION

The novel process of the invention for the recovery of rhodium from aqueous solutions of rhodium complex compounds comprises adding a molar excess of a water-soluble salt of an organic carboxylic acid of 7 to 22 carbon atoms to an aqueous solution of a rhodium complex compound, treating the solution with an oxidant at 50 to 200° C. and recovering the rhodium as a water-insoluble compound.

The procedure of the invention is particularly suitable for the recovery of rhodium from rhodium complexes which are soluble in water and are used as the catalyst phase in the hydroformylation of olefins. Surprisingly, the process permits the rhodium generally present in low concentration to be recovered with great selectivity from the aqueous solution in a form which permits direct re-use of the rhodium as a catalyst constituent.

The solutions introduced into the recovery process contain the rhodium complex and excess complex ligands as well as their degradation and conversion products dissolved in water. The rhodium complex corresponds to the formula $HRh(CO)_xL_{4-x}$ wherein L is a water-soluble complex ligand and x is an integer from 1 to 3. The water-soluble complex ligands are preferably phosphines of the formula

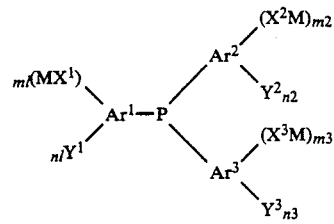

wherein $Ar^1$, $Ar^2$ and $Ar^3$ individually are phenyl or naphthyl, $Y^1$, $Y^2$, $Y^3$ individually are selected from the group consisting of straight-chain or branched alkyl of 1 to 4 carbon atoms, alkoxy of 1 to 4 carbon atoms, halogen,—OH,—CN,—$NO_2$ and $R^1R^2N$, $R^1$ and $R^2$ are each a straight-chain or branched alkyl of 1 to 4 carbon atoms; $X^1$, $X^2$, $X^3$ individually are a carboxylate —(-COO—) and/or sulfonate-($SO_3$—) , $n_1$, $n_2$, $n_3$ are the same or different whole numbers from 0 to 5, M is an alkali metal ion, equivalent of an alkaline earth metal or zinc ion or ammonium or quaternary alkyl ammonium ion of the formula wherein $N(R^3R^4R^5R^6)^+$, wherein $R^3$, $R^4$, $R^5$, $R^6$ are individually straight-chain or branched alkyl groups of 1 to 4 carbon atoms, and $m_1$, $m_2$, $m_3$ are the same or different whole numbers from 0 to 3, at least one number $m_1$, $m_2$ or $m_3$ being equal to 1 or higher than 1.

The rhodium complex is present in a concentration of 10 to 2000, particularly from 80 to 800, preferably 100 to 200 weight ppm and the aqueous solution contains 0 5 to 15, particularly 0.7 to 10, preferably 0.8 to 2.0% by weight of water-soluble complex ligands based on the aqueous solution. Degradation and conversion products of the water-soluble complex ligands are also still present in the solution and these include phosphine oxides and phosphine sulfides containing organic substituents, sulfonic acids, phosphine acids, carboxylic acids and their salts. Their concentration is 1 to 15, particularly 3 to 12, preferably 5 to 10% by weight, based on the aqueous solution. The salt residue calculated as a dry substance is 1.5 to 30, particularly 3.7 to 20 and preferably 5.8 to 15% by weight, based on the aqueous solution. Salt residue is understood to be the sum of all salt-like constituents, i.e. the rhodium complex ligands and their degradation and conversion products.

In the case of a hydroformylation catalyst, the aqueous solution exhibits a total of 0.15 to 4.0, particularly 0.8 to 3.0 and preferably 1.0 to 1.5% by weight of organic constituents, based on the aqueous solution. These include the olefin used, aldehydes, alcohols, aldols, condensation products and, if desired, solubilizers. The task of the solubilizers is to change the physical properties of the boundary surfaces between the organic, olefin-containing phase and the aqueous catalyst phase and to promote the transfer of the organic reactants to the catalyst solution and that of the water-soluble catalysts system to the organic phase.

According to the invention, the aqueous solution containing the rhodium complex is mixed and heated with the water-soluble salt of an organic carboxylic acid in molar excess to the rhodium. After the given temperature has been attained, oxidation is performed and the rhodium occurs as a water-insoluble rhodium carboxylate which can be removed directly. However, it can also be dissolved in a water-soluble organic solvent to facilitate separation of the rhodium carboxylate from the aqueous phase.

Examples of salts of organic carboxylic acids of 7 to 22 carbon atoms, preferably salts of organic carboxylic acids of 8 to 13 carbon atoms are salts of aliphatic, cycloaliphatic, aromatic and/or araliphatic carboxylic acids. Salts of monocarboxylic acids of the aliphatic, cycloaliphatic, aromatic and/or araliphatic series are well suited, particularly salts of branched aliphatic monocarboxylic acids and preferably salts of 2-ethylhexanoic acid, of the isononanoic acid (prepared by the hydrohydroformylation of diisobutylene and the subsequent oxidation of the product) and/or the isotridecanoic acid (prepared by the hydroformylation of tetrapropylene and subsequent oxidation of the hydroformylation product). Also, salts of phenylacetic acid and α and β -naphthoic acid have proved to be useful.

The use of alkali metal salts and/or ammonium salts of carboxylic acid, particularly sodium and/or potassium salts, preferably sodium salts, are preferred.

20 to 500, particularly 40 to 300, and preferably 50 to 200 moles of carboxylic acid salt are added to the aqueous solution per g-atom of rhodium The ratio of carboxylic acid to rhodium also depends on the rhodium concentration present in the aqueous solution. A low rhodium content permits the use of the carboxylic acid salt—according to its solubility—in particularly high excess while higher rhodium concentrations lead to correspondingly lower ratios of carboxylic acid salt to rhodium.

The salt of the carboxylic acid can be added to the aqueous solution before heating, but it is also possible to add it while the temperature necessary for oxidation is being attained or after it has been reached. The decisive factor is merely that the salt of the carboxylic acid is already present during oxidation as later addition of the salt leads to unforeseeably worse results. Moreover, it must be ensured that the salt residue does not exceed an upper limit. If the aqueous solution to be worked up contains more than 30% by weight of the salt residue based on the aqueous solution, the rhodium yield falls considerably and it is no longer possible to effectively perform the process of the invention.

The aqueous solutions are oxidized at temperatures from 50 to 200, particularly 60 to 160 and preferably 80 to 140° C. and it is necessary to conduct the oxidation at elevated temperatures to achieve a complete conversion. If the temperature is below 50° C., the yields of recovered rhodium fall and a considerable portion of the rhodium remains in the aqueous phase.

Pure oxygen, oxygen-containing gas mixtures and, particularly air are used as oxidants. However, it is also possible to employ other oxidants such as hydrogen peroxide, hydrogen peroxide-forming compounds, hypochlorite, chromates an permanganates, with hydrogen peroxide being particularly suitable.

Oxidation can be carried out both at normal pressure and at elevated pressure and suitable pressures are 0.1 to 2.0, particularly 0.2 to 1 and preferably 0.3 to 0.7 MPa. The pH of the aqueous solution is 4 to 8, particularly 5.0 to 7.5 and preferably 5. 5 to 7.0. In the case of hydroformylation in the aqueous phase, subordinate amounts of aldehydes are continually present from which carboxylic acids form during oxidation and it is recommended to measure the pH-value during oxidation and, if necessary, adjust it to the required range.

If the presence of carboxylic acids formed from the aldehydes is to be avoided completely, the starting aqueous solution is subjected to a distillation or the organic products are forced over, e.g. by passing through superheated steam before oxidation takes place. The result of the oxidation is that not only the complex ligand present in excess is attacked but also the rhodium complex itself with the ligand being converted to a form which is no longer suitable for the formation of complexes. The corresponding phosphine oxides are formed from the above-mentioned phosphines and the rhodium complex originally present breaks down.

During the oxidation, water-insoluble rhodium compounds (rhodium carboxylates) are formed and separate as an oily layer or as droplets and removal can be performed by simple phase separation with the lower aqueous phase being removed. However, it is helpful to promote rhodium recovery by the addition of water-insoluble, organic solvents which can dissolve the water-insoluble rhodium compound. The organic solvent can be added either before or during oxidation. It has proved particularly successful to add the solvent to the reaction mixture after oxidation at 10 to 100, in particularly 20 to 70, and preferably 40 to 60° C.

Suitable organic solvents are benzene, toluene, xylene, cyclohexane, aliphatic carboxylic acids and carboxylic acid esters, aliphatic and cycloaliphatic ketones of 5 to 10 carbon atoms. Toluene and xylene are particularly suitable with the use of toluene being preferred.

The upper phase containing the organic solvent and the water-insoluble rhodium compound is separated from the bottom, aqueous phase and phase separation is conducted at 10 to 100, particularly 20 to 70 and preferably 40 to 60° C. To complete the rhodium recovery, the separated aqueous phase is, if necessary, re-extracted with fresh organic solvent and the phases are separated. This procedure can be repeated several times but generally, it is sufficient to extract the aqueous phase one to three times.

The organic phases are mixed together and can be used directly as catalyst constituents without any aftertreatment. It is also possible to extract the rhodium carboxylate present in the organic solvent with aqueous solutions containing a phosphine ligand and to use this extract as a catalyst solution. The process of the invention permits about 90 to 95% of the rhodium originally present to be separated from the aqueous solution and the remaining rhodium stays in the aqueous phase and can be recovered separately.

In the following examples there are described several preferred embodiments to illustrate the invention However, it is to be understood that the invention is not intended to be limited to the specific embodiments.

EXAMPLE 1

300 g of solution A (see Table I) and 18.55 g of an aqueous sodium 2-ethylhexanoate solution (65.8% by weight sodium salt based on the solution) were oxidized in a glass autoclave with stirring at 100° C. and a pressure of 0.4 to 0.45 MPa through the introduction of 150 standard liters of air. The reaction was completed after 2 hours and the contents of the autoclave were cooled. An oily layer formed which was removed by extraction with 60 g of toluene and a second extraction with 50 g of toluene whereby 8.2% of the rhodium originally present remained in the aqueous solution. The experiment was repeated under the same conditions and the aqueous solution contained 7.5% of the rhodium originally present.

COMPARATIVE EXAMPLE 2

Example 1 was repeated with the only difference being that the aqueous sodium 2-ethylhexanoate solution was not added at 100° C. until oxidation has been completed. The aqueous solution was then cooled and extracted twice with toluene and 75.1% by weight of the rhodium originally present remained in the aqueous solution.

EXAMPLE 3

300 g of solution B (see Table I) were poured into a glass autoclave (volume: 1 liter) together with 8.0 g of an aqueous sodium 2-ethylhexanoate solution (65.8% by weight sodium salt based on the solution) and 5.0 g of 2-ethylhexanoic acid. With stirring, the mixture was heated to 100° C. and after the said temperature had been reached, oxidation was initiated by the addition of hydrogen peroxide. 10 g of 30% by weight of hydrogen peroxide were added over a period of 5 minutes and the mixture was allowed to stand at the pressure which automatically formed Oxidation was completed after 30 minutes and the contents of the glass autoclave were cooled. The aqueous solution was first mixed with 60 g of toluene, and after separation of the toluene phase, the aqueous phase was re-extracted with 50 g of toluene. After separation of the toluene phase, 6.2% of the rhodium originally present remained in the aqueous phase.

COMPARATIVE EXAMPLE 4

Example 3 was repeated but instead of 8.0 g of aqueous sodium 2-ethylhexanoate solution 3.8 g of sodium butyrate were used and instead of 5.0 g of 2-ethylhexanoic acid, 3.1 g of butyric acid were used. After extraction with toluene as described in Example 3, 90.7% of the rhodium originally present remained in the aqueous solution.

EXAMPLE 5

300 g of aqueous solution B (see Table I) used in Example 3 were poured into a glass autoclave (volume: 1 liter) together with 8.0 g of a sodium 2-ethylhexanoate solution (65.8% by weight sodium salt based on the solution). With stirring, the mixture was heated to 100° C. and after the said temperature had been reached, oxidation was performed by the introduction of pure oxygen at a pressure of 0.5 MPa. Oxidation was completed after 4 hours and the mixture was, as described in Example 3, cooled and extracted with toluene and 4.8% of the rhodium originally present remained in the aqueous solution.

Another experiment conducted under the same conditions gave an aqueous solution containing 6.5% of the rhodium originally present.

EXAMPLE 6

Example 5 was repeated with the only difference being that 5 g of 2-ethylhexanoic acid were added in addition to the sodium 2-ethylhexanoate solution. Oxidation was again carried out at 100° C. but over a period of 2 hours. Then the mixture was, as described in Example 3, cooled and extracted with toluene and 4.7% of the rhodium originally present remained in the aqueous solution.

Another experiment under the same conditions but with oxidation lasting 1 hour gave an aqueous solution containing 6.0% of the rhodium originally present.

EXAMPLES 7 a to i 300 g of solution C (see Table I) were mixed with the amounts of carboxylic acid and NaOH mentioned in Table 2 and the mixtures were poured into a glass autoclave (volume: 1 liter). With stirring, the mixture was heated to 100° C. and after the said temperature had been reached oxidation was performed by the introduction of air at a pressure of 0.4 MPa. The amount or air introduced is set forth in Table 2 and oxidation was completed after 4 hours. The contents of the glass autoclaves were worked up as described in Example 1 and the amount of rhodium remaining in the aqueous solution after extraction is set forth in Table 2 (rhodium in waste water).

EXAMPLES 8 a to g 300 g of solution D (see Table I) were mixed with the amounts of sodium 2-ethylhexanoate (.65 8% by weight sodium salt based on the solution) mentioned in Table 3 and the mixture was poured into a glass autoclave (volume: 1 liter). The pH value of Table 3 was adjusted by the addition of NaOH or $H_2SO_4$ and maintained during the oxidation. With stirring, the solution was oxidized at 100° C. and a pressure of 0.45 MPa by the introduction of 150 standard liters of air. The reaction was completed after 2 hours and as described in Example 1, an oily layer formed which was removed by extraction with toluene. The amount of rhodium remaining in the aqueous solution after extraction is set forth in Table 3.

EXAMPLE 9

300 g of solution D (see Table 1) were distilled to remove any organic products still present and distillation took place at normal pressure. At a head temperature of 100° C., 78.3 g of product (corresponding to 26.1% by weight based on the aqueous solution) were removed. The remaining distillation residue was made up to 300 g with distilled water and worked up as described in Examples 8a to g. Table 3 gives data on the pH, amount of sodium 2-ethylhexanoate (as 65.8% by weight sodium salt based on the solution) and the amount of rhodium in the waste water.

TABLE 1 in weight-%; Rh in ppm

| Constituents | Solution | | | |
|---|---|---|---|---|
| | A | B | C | D |
| TPPTS | 2.80 | 0.22 | 3.13 | 1.70 |
| TPPOTS | 2.45 | 1.72 | 2.0 | 1.73 |
| TPPSTS | — | 0.03 | 0.02 | — |
| TPPDS | 0.14 | <0.01 | 0.2 | 0.04 |
| TPPODS | 0.50 | 0.48 | 0.42 | 0.38 |
| TPPSDS | 0.02 | — | 0.02 | 0.03 |
| BSNS | 0.97 | 0.92 | 0.55 | 0.55 |
| rem. salts* | 5.12 | 7.19 | 2.33 | 4.23 |
| Rhodium | 135 ppm | 165 ppm | 174 ppm | 124 ppm |

*as residue (dry substance) determined by flash distillation (95° C./15 Torr (2,25 kPa)).

In the following table the abbreviations mean:
TPPTS: Na$_3$-triphenylphosphine trisulfonate
TPPOTS: Na$_3$-triphenylphosphine oxide trisulfonate
TPPSTS: Na$_3$-triphenylphosphine sulfide trisulfonate
TPPDS: Na$_2$-triphenylphosphine disulfonate
TPPODS: Na$_2$-triphenylphosphine oxide disulfonate
TPPSDS: Na$_2$-triphenylphosphine sulfide disulfonate
BSNS: Na-benzenesulfonate

TABLE 2

| Example No. | Carboxylic acid | Base | Vol. air NL | Rhodium in waste water % |
|---|---|---|---|---|
| a | 15.4 g n-C$_5$-acid | 3.0 g NaOH | 200 | 73.2 |
| 7 b | 15.4 g n-C$_5$-acid | 3.0 g NaOH | 237 | 66.1 |
| 7 c | 19.53 g n-C$_7$-acid | 3.0 g NaOH | 248 | 31.2 |
| 7 d | 25.84 g n-C$_{10}$-acid | 3.0 g NaOH | 206 | 10.3 |
| 7 e | 14.51 g 2-Ethylhexanoic acid | 2.636 g NaOH | 190 | 3.6 |
| 7 f | 19.51 g 2-Ethylhexanoic acid | 2.636 g NaOH | 200 | 4.8 |
| 7 g | 17.0 g Iso-C$_9$-acid$^{(1)}$ | 3.05 g NaOH | 266 | 3.5 |
| 7 h | 21.35 g Iso-C$_{13}$-acid$^{(2)}$ | 3.05 g NaOH | 182 | 5.7 |

TABLE 2-continued

| Example No. | Carboxylic acid | Base | Vol. air NL | Rhodium in waste water % |
|---|---|---|---|---|
| 7 i | 26.71 g Iso-C$_{18}$-acid$^{(3)}$ | 3.05 g NaOH | 160 | 55.6 |

$^{(1)}$Prepared by the hydroformylation of diisobutylene and subsequent oxidation.
$^{(2)}$Prepared by the hydroformylation of tetrapropylene and subsequent oxidation.
$^{(3)}$Main component 2,2,4,8,10,10-hexamethyl undecanoic carboxylic acid-7

TABLE 3

| Example No. | pH-value | Na-2-ethyl-hexanoate(g) | Rhodium in waste water (%) |
|---|---|---|---|
| 8 a | 3.3 | 14.45 | 26 |
| 8 b | 4.5 | 14.45 | 13.6 |
| 8 c | 5.8 | 14.45 | 6.2 |
| 8 d | 6.2 | 14.45 | 6.1 |
| 8 e | 6.6 | 13.8 | 7.7 |
| 8 f | 8.7 | 14.45 | 33.5 |
| 8 g | 10.3 | 14.45 | 36.8 |
| 9 | 6.9 | 13.8 | 6.7 |

Various modifications of the process of the invention may be made without departing from the spirit or scope thereof and it is to be understood that the invention is intended to be limited only as defined in the appended claims.

What we claim is:

1. A process for the recovery of rhodium from aqueous solutions of rhodium complex compounds comprising adding a stoichiometric excess of a water-soluble salt of an organic carboxylic acid of 7 to 22 carbon atoms to an aqueous solution of a rhodium complex compound having a pH of 4 to 8, treating the solution with an oxidant at 50 to 200° C. to form water-insoluble rhodium compound and separating the rhodium compound therefrom.

2. The process of claim 1 wherein the salt is that of a saturated, straight-chain or branched monocarboxylic acid.

3. The process of claim 1 wherein the carboxylic acid has 8 to 13 carbon atoms.

4. The process of claim 1 wherein the salt of the carboxylic acid is an alkali metal salt.

5. The process of claim 1 wherein the oxidant is oxygen or an oxygen-containing gas.

6. The process of claim 1 wherein air is used as an oxidant.

7. The process of claim 1 wherein the aqueous solution is treated with an oxidant at a pressure of 0.1 to 2.0 MPa.

8. The process of claim 1 wherein the separated water-insoluble rhodium compound is extracted with a water-insoluble organic solvent.

9. The process of claim 8 wherein the organic solvent is toluene.

* * * * *